Figure 1:
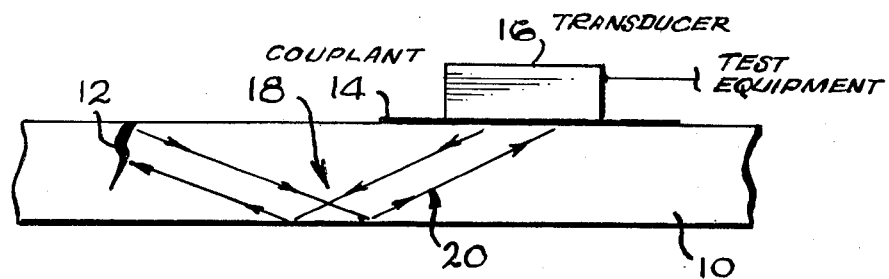

United States Patent [19]  [11] 3,939,101
Molina  [45] Feb. 17, 1976

[54] COMPOSITION FOR ULTRASONIC INSPECTION OF OBJECTS AND METHOD FOR EMPLOYING SAME

[75] Inventor: Orlando G. Molina, Westminster, Calif.

[73] Assignee: Rockwell International Corporation, El Segundo, Calif.

[22] Filed: Feb. 21, 1974

[21] Appl. No.: 444,213

Related U.S. Application Data

[62] Division of Ser. No. 295,059, Oct. 4, 1972, Pat. No. 3,826,127.

[52] U.S. Cl.......................... 252/408 R; 252/301.2 P
[51] Int. Cl.$^2$.................... G01N 29/04; C09K 3/00
[58] Field of Search............. 252/408, 301.2 P, 315, 252/316, 317, 542, 524, 154, 155; 73/104, 71.5 US, 67.5 R

[56] References Cited
UNITED STATES PATENTS

| | | | |
|---|---|---|---|
| 3,716,494 | 2/1973 | Molina | 252/317 X |
| 3,806,460 | 4/1974 | Mukai et al. | 252/542 X |
| 3,838,160 | 9/1974 | Molina | 252/408 X |

*Primary Examiner*—Benjamin R. Padgett
*Assistant Examiner*—David Leland
*Attorney, Agent, or Firm*—Charles T. Silberberg; L. Lee Humphries

[57] ABSTRACT

Composition for ultrasonic inspection of surface and subsurface flaws and discontinuities in bodies, in the form of an aqueous gel containing an N-alkyl-2-pyrrolidone having a short alkyl chain, preferably N-methyl-2-pyrrolidone, a water soluble surfactant, e.g. a nonyl phenyl ether of polyethylene glycol, and silica, preferably in fine powder form, suspended uniformly in the gel. The composition or gel is applied to a surface of a body such as a metal aircraft structural part, and a probe or transducer of an ultrasonic testing device is contacted or pressed against the gel and the transducer is caused to move or slide in various directions on the gel to transmit ultrasonic energy through the gel and the object, to inspect the object and locate any surface or subsurface flaws or discontinuities.

16 Claims, 2 Drawing Figures

COMPOSITION FOR ULTRASONIC INSPECTION OF OBJECTS AND METHOD FOR EMPLOYING SAME

This is a division of application Ser. No. 295,059 filed Oct. 4, 1972, now U.S. Pat. No. 3,826,127.

This invention relates to the inspection of surface and subsurface flaws and discontinuities in objects by ultrasonic nondestructive testing, and is particularly concerned with the provision of a novel ultrasonic couplant composition to provide good ultrasonic transmission and particularly adapted for use for such ultrasonic inspection, and also to a method of ultrasonic inspection employing such novel composition.

Ultrasonic nondestructive testing of bodies such as metal parts has been developed. This is a method which utilizes UHF (ultra-high frequency) sound waves to detect discontinuities in parts. An ultrasonic testing device is employed, in which a probe or transducer is placed in contact with a surface of the part to be inspected. Ultrasonic waves are generated by applying a pulsed oscillating voltage from a pulser to a transducer (piezoelectric crystal). When the transducer is electrically excited and is adequately coupled to a part being inspected, an ultrasonic wave passes into the part. A change in acoustic properties of the part (surface and subsurface cracks, discontinuities, part surfaces, interfaces) reflects the wave back to the transducer. The reflected wave mechanically stresses the transducer and the transducer generates electrical charges. The electrical signals are applied to an amplifier circuit with the ultrasonic instrument, where they are amplified and displayed on a CRT (cathode-ray tube).

In the above procedure, a couplant is required to be applied to a surface of the object to be tested, to provide an effective medium for ultrasonic transmission between the transducer or probe applied to the surface of the body, and the body undergoing nondestructive testing. Thus, the primary purpose of couplants is to provide a suitable ultrasonic path between the transducer and part being inspected. Air is a poor conductor of ultrasonic energy. The couplant also fills in and smooths out irregularities of a part's surface and aids in movement of the transducer. A further purpose of the couplant is to serve as an acoustic impedance matching medium. The closer the couplant acoustic impedance matches that of the part being inspected, the better the ultrasonic wave transfer.

Ultrasonic coupling compositions which have been employed to date by the industry include for example, water, glycerin, light oil and petroleum jelly or grease. These materials have been used in the past basically because of their relatively good ultrasonic transmission characteristics. However, none of the prior art couplants such as those noted above have all of the desirable features required for efficient ultrasonic inspection of parts. Thus, for example, water and glycerin are corrosive to certain metals. Oils and greases usually contaminate the surface of the parts to be tested, making it necessary to degrease the parts after testing. Further, in those cases where the parts comprise titanium or its alloys, the degreasing is required, the use of highly flammable solvents is necessary for this purpose, since the usual chlorinated solvents employed for degreasing are detrimental to titanium and cannot be employed.

It is accordingly the chief object of the present invention to provide an ultrasonic couplant composition, that is a composition for use in ultrasonic inspection of parts, having excellent ultrasonic transmission, which is noncorrosive to metals, particularly titanium, aluminum and steel, and their various alloys, is nonflammable, odorless and essentially nontoxic, can be simply applied to a part to be tested and the part surface oriented in a horizontal, vertical or overhead position, without dripping of the composition, and while permitting a probe or transducer to remain adhered to the couplant composition regardless of the orientation of the part surface, such couplant composition being essentially non-hygroscopic, easily removable from the part surface such as by removal with water, and being reusable and relatively inexpensive to manufacture. Another important characteristic of the couplant composition sought according to the invention is the ability of the couplant composition to be traced for complete removal, as for example by incorporation of a fluorescent dye, any observed traces of which will indicate the presence of any residual couplant and assure complete removal thereof upon completion of inspection.

The above objects and advantages are obtained according to the invention by the provision of an ultrasonic couplant composition comprising an aqueous gel containing an N-alkyl-2-pyrrolidone wherein the alkyl group contains from 1 to 4 carbon atoms, a water soluble surfactant and silica suspended in the gel.

In preferred practice, as will be pointed out in greater detail hereinafter, the pyrrolidone particularly effective for this purpose has been found to be N-methyl-2-pyrrolidone, and the preferred surfactant is a water soluble nonionic surfactant or wetting agent, such as the nonyl phenyl ether of polyethylene glycol. The silica component preferably is in the form of a fine powder, distributed uniformly in the aqueous gel. Preferably, the respective components of the composition, including the pyrrolidone, surfactant, silica and water are employed in certain proportions, as pointed out in detail hereinafter. The ultrasonic couplant composition or gel of the invention has essentially all of the advantages stated in the above objects, and is essentially neutral, rendering it highly compatible with metals and metal alloys, particularly those employed in aircraft structural parts, notably aluminum, titanium and steel. The composition is moreover essentially nontoxic and can be readily handled by personnel, and is economical.

As will be further pointed out in greater detail below, the above-noted components of the composition can be readily mixed, forming a gel of suitable viscosity almost immediately, and the gel can be stored in closed containers without degradation, over relatively long periods, for use as desired.

The pyrrolidone component employed in the ultrasonic couplant composition of the invention functions as the main solvent of the composition, and promotes wetability of the gel composition with respect to the surface of an object to be tested, such as a metal part, and functions as a stabilizer for the gel. The pyrrolidone component which is useful according to the present invention is an N-alkyl-2-pyrrolidone wherein the alkyl group has a short carbon chain of from 1 to 4 carbon atoms. Examples of such groups are methyl, ethyl, propyl, isopropyl, butyl and isobutyl. Specific examples of these compounds are N-methyl-2-pyrrolidone, N-ethyl-2-pyrrolidone, N-propyl-2-pyrrolidone, N-isopropyl-2-pyrrolidone, N-butyl-2-pyrrolidone, and N-isobutyl-2-pyrrolidone.

A lower N-alkyl substituted pyrrolidone having the foregoing general structure and which is especially preferred in practicing the invention is N-methyl-2-pyrrolidone.

N-vinyl-2-pyrrolidone, as contrasted to the above-noted N-alkyl-2-pyrrolidones, has been found unsuitable for use in the invention composition. Such N-vinyl-2-pyrrolidone presents problems of water washability, and in addition the N-vinyl-2-pyrrolidone, particularly upon contact with or addition of water, emits a highly obnoxious odor, rendering it highly unsuitable for handling by operating personnel.

The N-alkyl-2-pyrrolidone hereof, particularly the N-methyl-2-pyrrolidone, can be employed in varying amounts in producing the gel composition hereof, and generally is employed in an amount ranging from about 10 to about 40 percent, preferably about 15 to about 35 percent, by weight of the composition.

The water soluble surfactant component of the ultrasonic couplant composition hereof functions as a gel forming wetting agent or gel promoter. Thus, the water soluble surfactant hereof aids in the formation of a gel upon the addition of water to the pyrrolidone solvent. The choice of water soluble surfactant which can be employed may vary among commercially available surfactants, a water soluble nonionic detergent or wetting agent being particularly effective. A hydrophilic nonionic detergent containing ether-oxygen groups, is preferred in combination with the pyrrolidone, e.g. N-methyl-2-pyrrolidone, a particularly effective surfactant or detergent of this type being marketed as Tergitol nonionic NPX, although other nonionic detergents such as Tergitol nonionic TMN and Aerosol OT 75 percent also can be employed. Tergitol nonionic NPX is a nonyl phenyl ether of polyethylene glycol containing 10.5 mols of ethylene oxide and having the general formula $C_9H_{19}C_6H_4O(CH_2CH_2O)_{10.5}H$. Tergitol TMN is a trimethyl nonyl ether of polyethylene glycol containing 6 mols of ethylene oxide and has the formula $(CH_3)_3C_9H_{16}O(CH_2CH_2O)_6H$. Aerosol OT 75 percent is a 75 wt percent solution in water of dioctyl sodium sulfo-succinate. Other nonionic surfactants are also usable in the ultrasonic couplant composition disclosed herein to produce essentially the same results, provided that such surfactants are sufficiently hydrophilic in nature and do not require the use of an inordinate amount of silica to maintain the physical integrity and strength of the gel, as pointed out more fully below.

The water soluble surfactant component also may be employed in varying proportions, but generally is employed in an amount ranging from about 10 to about 35 percent, preferably about 15 to about 30 percent, by weight of the composition.

The silica component of the couplant composition hereof functions when uniformly dispersed in the composition, to form a colloid dispersion in the gel which provides gel strength and physical integrity, and maintains the gel stable at varying temperatures, particularly at elevated temperature, e.g. up to about 125°F or higher. Thus the gel remains stable when applied to an object or a part which is at elevated temperature. The silica preferably is employed in an extremely fine powder form. Thus, in preferred practice such fine powdered silica can have a particle size ranging from about 0.007 to about 0.050 micron (about 70 to about 500 angstroms), and under such conditions is an extremely fluffy, snow-white powder of extremely low bulk density. A commercially available form of this component having the above fine particle size is marketed as Cab-O-Sil M-5 by Cabot Corporation. Such Cab-O-Sil has an enormous external area, 1 gram of Cab-O-Sil M-5 having about 400 square meters of surface area. Cab-O-Sil M-5 is a submicroscopic fire-dry fumed silica different in structure from precipitated silicas or silica gels.

An important criterion of the composition of the invention is the formation of a clear gel which is transparent so that after application of the gel to a part surface one can see the surface of the part through the gel, the fine silica dispersion essentially permitting such transparency in the gel. Also, the fine powdered silica preferably employed is essentially nonabrasive and tends to impart lubricity to permit easy spreading of the gel in a thin layer over the part surface.

The silica component can also be employed in varying amounts, but generally is employed in an amount ranging from about 10 to about 40 percent, preferably about 10 to about 25 percent, by weight of the composition.

Water is employed in the invention composition to form the aqueous gel matrix, and is utilized, in conjunction with the pyrrolidone, water soluble surfactant and silica components, as an extender and gel promoter. Although tap water can be employed, deionized water is preferred since tap water may contain salts and minerals which may be corrosive to metals to be tested.

Water is employed also in varying amounts dependent on the proportions of the other components employed, particularly the pyrrolidone and surfactant components, but generally the water is employed in an amount ranging from about 10 to about 50 percent, preferably about 15 to about 40 percent, by weight of the composition.

As previously noted, it is often desirable to be able to check the part surface for the presence of residual gel, after an inspection of the part has been completed and the bulk or major portion of the gel has been removed from the surface. This can be accomplished by incorporating either a daylight visible dye or a fluorescent dye into the gel or couplant composition of the invention, and viewing the surface of the part under proper lighting conditions to detect any traces of the gel as indicated by the presence of colored or fluorescent indications or smears imparted by the presence of the dye in the composition. For this purpose, it is preferred to incorporate as an optional component a fluorescent dye which is either colorless or only lightly colored when viewed by visible light, but which provides a bright fluorescent color when viewed under fluorescent or "black" light. Thus the presence of the dye in the gel still renders the gel clear in white or ordinary daylight so that the part surface can be viewed through the layer of gel applied to the part surface.

Various types of fluorescent dyes can be employed including for example the dye marketed as Fluorol 7GA as well as other fluorescent dyes such as those marketed as Calcofluor Yellow, Asosol Brilliant Yellow 6GF, Rhodanine B, Rhodanine 6GDN, Calcofluor White RW, Blancophor White AW, Auramine and Eosine G. The above-noted Rhodanine dyes, Auramine and Eosine G fluoresce in a color range from greenish yellow to red. There can also be employed nonfluorescent or daylight type dyes such as azo type dyes, e.g. xyleneazo-beta-naphthol, Mefford No. 322 dye, believed to be o-tolueneazoxyleneazo-beta-naphthol, and the azo dyes marketed as Oil Red "O" and Sudan Red.

These dyes can be employed where daylight or white light is only available. Here also it is preferred to employ those daylight dyes which are light colored and which permit the gel to be sufficiently transparent to permit viewing the surface of the part to which the gel is applied, through the gel layer or film.

The amount of the optional dye component, e.g. fluorescent or daylight dye, employed, can vary, but it is generally employed in a small amount ranging from about 0.2 to about 2 percent, preferably about 0.2 to about 1.5 percent, by weight of the composition.

Illustrative examples of ultrasonic couplant compositions according to the invention, but not in limitation thereof, are set forth in the table below, the amounts of the respective components being expressed in terms of per cent by weight.

In formulating the ultrasonic couplant composition of the invention, the order of addition of the components is not essential, but usually the liquids, including the pyrrolidone, water soluble surfactant and water are first mixed or added together and the silica component then added to the resulting solution. Where the optional dye component is added, it can be incorporated for example with the liquids, and prior to introduction of the silica, although if desired the dye can be added last. Upon mixing of all of the components, the composition initially forms a gel which remains stable after applied to the part for purposes of ultrasonic inspection.

In employing the ultrasonic couplant composition or gel according to the invention, for purposes of ultrasonic inspection of a part, the part employed, if neces- EXAMPLES (% by weight)

| Component | 1 | 2 | 3 | 4 | 5 | 6 | 7 | 8 | 9 | 10 | 11 |
|---|---|---|---|---|---|---|---|---|---|---|---|
| N-methyl-2-pyrrolidone | 30.75 | 20.0 | 40.0 | 32 | 15.0 | 10.0 | 30.0 | 25.0 | 20.0 | 35.0 | 10.0 |
| Deionized H$_2$O | 29.0 | 40.0 | 20.0 | 28 | 45.0 | 50.0 | 29.0 | 24.0 | 32.0 | 23.0 | 14.0 |
| Fumed silica | 17.25 | 18.0 | 20.0 | 10.0 | 30.0 | 10.0 | 22.0 | 24.0 | 20.0 | 15.0 | 40.0 |
| Tergitol Nonionic NPX | 22.0 | 21.5 | 20.0 | 29.5 | 10.0 | 29.5 | 18.0 | 26.0 | 28.0 | 26.0 | 35.0 |
| calcofluor white RW | 0.5 | — | — | 0.5 | — | — | — | — | — | 1.0 | 0.5 |
| Fluorol 7GA | 0.5 | 0.5 | — | — | — | 0.5 | — | 1.0 | — | — | 0.5 |
| | 100.0 | 100.0 | 100.0 | 100.0 | 100.0 | 100.0 | 100.0 | 100.0 | 100.0 | 100.0 | 100.0 |

Particularly effective compositions according to the invention for ultrasonic nondestructive inspection, are those of Examples 1, 2, 3, 8 and 11 of the above table.

The following are additional examples of illustrative couplant compositions according to the invention, wherein the N-methyl-2-pyrrolidone, the Tergitol nonionic NPX and the deionized water of certain of the compositions of the examples of the above table, are replaced by equivalent components according to the invention as described above.

EXAMPLE 12

| | (% by weight) |
|---|---|
| N-ethyl-2-pyrrolidone | 30 |
| Deionized water | 30 |
| Fumed silica | 18 |
| Tergitol nonionic TMN | 22 |
| | 100 |

EXAMPLE 13

| | (% by weight) |
|---|---|
| N-propyl-2-pyrrolidone | 20 |
| Tap water | 40 |
| Fumed silica | 18 |
| Tergitol nonionic NPX | 22 |
| | 100 |

EXAMPLE 14

| | (% by weight) |
|---|---|
| N-butyl-2-pyrrolidone | 10 |
| Deionized water | 34 |
| Powdered silica | 25 |
| Aerosol OT 75% | 30 |
| Fluorol 7GA | 1 |
| | 100 |

EXAMPLE 15

| | (% by weight) |
|---|---|
| N-methyl-2-pyrrolidone | 25 |
| Deionized water | 25 |
| Powdered silica | 24 |
| Tergitol nonionic NPX | 26 |
| | 100 | sary, can first be cleaned to remove any contaminants from the part surface. The ultrasonic couplant gel of the invention is readily applied over the surface area of the part to be inspected by ultrasonic transmission through the part. For this purpose the gel can be dispensed and applied to the part surface to provide a thin layer of couplant, by any suitable means such as by the hand, spatula or brush. The probe or transducer of the ultrasonic test equipment is then pressed into contact with the gel on the surface of the part, and is readily moved as by sliding over the gelled surface in any direction necessary for inspection of cracks, flaws, or discontinuities such as part surfaces or interfaces, which may be contained on the surface of the part or within the part. The ultrasonic system for this purpose includes means in the form of a probe or transducer to generate ultrasonic energy, a couplant according to the present invention, and an ultrasonic instrument. The latter instrument contains suitable circuits, including a receiver-amplifier circuit and a CRT for displaying electrical signals generated by the transducer when discontinuity echoes are present, corresponding to any flaws, cracks or discontinuities in the body, as the transducer is moved over the gel on the surface of the body.

The sensitivity of the ultrasonic equipment employed should be such as to be capable of detecting the smallest defect which may be encountered in the part being tested. The thin layer or film of ultrasonic couplant gel of the invention formed on the surface of the part between the probe or transducer and the part surface maintains excellent ultrasonic transmission between the transducer and the part at all times. The presence of cracks, flaws, or discontinuities on the surface or within the body of the part being tested is detected by variations in noise signals received by the testing unit, and which can be indicated on the CRT display mechanism. If there is improper coupling between the transducer and the body being tested, there will be an absence of noise signals received by the test unit. By means of the ultrasonic testing equipment employed, in conjunction with the thin film of gel couplant according to the invention, on the surface of the body, the size of flaws, cracks or discontinuities on or in the test body, for example the length thereof as well as their orientation, can be detected.

The above-described ultrasonic test system and equipment is well known and since it forms no part of the present invention it is not described in detail herein. However, the use of the invention couplant composition in an ultrasonic inspection system for detecting cracks and defects in a part is schematically illustrated in the accompanying drawing.

Figure 2:
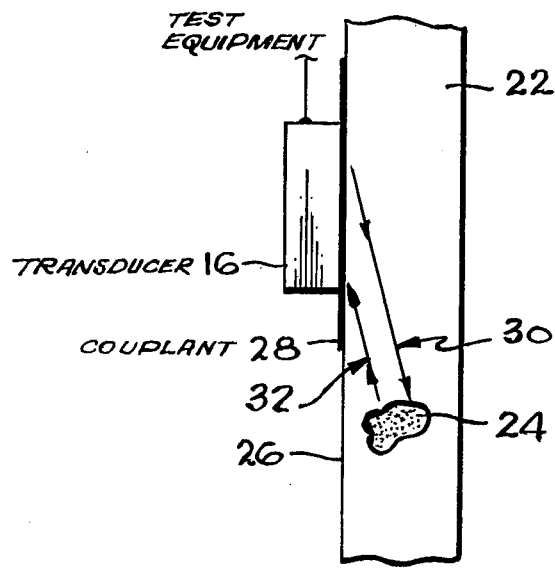

FIG. 1 of the accompanying drawing illustrates the detection of cracks and flaws in a metal part employing the ultrasonic couplant of the invention, and FIG. 2 illustrates practice of the invention utilizing the couplant composition hereof applied to a vertically disposed surface of a part for detection of any defects therein.

In FIG. 1, 10 represents a metal part containing cracks indicated at 12, which may be both surface cracks and internal cracks. The layer of couplant gel of the invention is shown at 14 and the transducer, indicated at 16, of the ultrasonic test equipment (not shown) is pressed into contact with the surface of the gel 14, and manually is made to slide on the gel surface into the proper location to detect cracks 12. When the transducer is electrically excited, an ultrasonic wave is transmitted through the gel layer 14, and such sound wave indicated at 18, impinging on the cracks 12, is reflected back through the part, as indicated at 20, to the transducer 16, which generates electrical signals indicating such cracks, which are amplified and displayed on a CRT (not shown) of the test equipment.

Similarly FIG. 2 shows a part 22 having an internal void as indicated at 24, the part being disposed in a vertical position. A gel couplant composition according to the invention, is applied to a vertical surface 26 of the part, in the form of a thin layer at 28, and the transducer, indicated at 16, of an ultrasonic test equipment is pressed into contact with the thin vertical layer of gel 28 on part surface 26. As seen in this embodiment, the gel layer 28 has sufficient viscosity to be maintained on the vertical surface of the part without dripping, and the transducer 16 can be maintained in position on the vertical gel surface without any support by the hand of the operator, simply by adherence ot the transducer to the gel layer. Upon excitation of the transducer the incident sound wave 30 is transmitted across the gel layer 28 and through the test body 22, and is reflected back at 32 by the discontinuity at the void or defect 24, to the transducer 16, and the resulting signal from the transducer indicating a change in acoustic properties corresponding to the discontinuity is displayed on the CRT of the inspection system.

It will be understood that the schematic illustrations in the drawing are intended only as illustrative of practice of the invention.

After the ultrasonic inspection is completed, the layer or film of couplant composition or gel can be scraped from the surface of the past by suitable means, and returned to the container for reuse, or such gel layer can be wiped clean with dry cloths followed by a water moistened wiping. Due to the N-alkyl-2-pyrrolidone vehicle and the water soluble surfactant contained in the gel, the gel can be readily removed from the part surface by the application of water thereto, as by a water spray.

Where the ultrasonic couplant composition or gel of the invention contains the optional fluorescent dye component, the surface area of the part from which the gel layer has been removed can be viewed under fluorescent or "black" light illumination to check for the presence of residual or trace amounts of the gel. Any such traces or residual gel will provide bright fluorescent indications, so that a final removal operation of the residual gel can then be performed in those specific areas in which the gel still remains. As previously noted, such excess or residual gel can be removed by water spraying since the gel is highly soluble in water.

Alternatively, in place of employing a fluorescent dye, a dye such as an azo dye which is visible by ordinary white light or daylight can be employed, and any residual gel indicated by any dye smears under ordinary visible light, can then be removed from the part surface in the manner noted above.

As previously indicated, the components of the ultrasonic couplant composition or gel of the invention can be varied, and the amounts thereof varied as described above to provide a formulation which has the desired viscosity for the particular purpose. Preferably, the viscosity of the gel is such that it can be readily applied by means noted above over the part surface to form a thin film or layer of the gel on the surface, and the ultrasonic transducer or probe can be readily moved or can readily slide on the gel surface from one selected area to another. It is particularly noteworthy that in addition to its ability to be readily applied, the ultrasonic couplant gel composition of the invention, due to its viscosity, can be employed on vertical and overhead surface applications without dripping of the composition, and the ultrasonic probe or transducer remains adhered to the gel-treated surface in horizontal, vertical and overhead surface applications, permitting the operator freedom of both hands for example to return to the ultrasonic console of the test equipment and make adjustments, when necessary.

The couplant composition or gel of the invention can be employed for ultrasonic nondestructive testing of all types of parts, particularly metal parts of aircraft such as titanium and aluminum wing skins, structural hardware such as bulkheads or wing spars of aircraft, and aluminum, steel or titanium castings. Such ultrasonic testing process employing the couplant composition of the invention can be used to detect so-called "unbonds," e.g. of a fusion welded airplane fuselage bulkhead. Thus the ultrasonic couplant composition of the invention can be employed to detect surface and subsurface flaws and discontinuities, for example cracks, voids and unbonds in the fusion welding to determine the nature and integrity of the welds.

The following are examples of practice of the invention employing the novel ultrasonic coupling composition hereof.

EXAMPLE 16

The composition of Example 1 above was applied by brushing to selected areas of an aluminum aircraft wing skin, to form a thin layer of the gel on the part surface. The transducer of an ultrasonic test equipment was pressed into contact with the surface of the gel and was moved by sliding in various selected directions over the gel along the surface of the part. Variations in noise signals on the CRT display unit of the test equipment indicated cracks and discontinuities in the part, and presenting an indication of the location, orientation and size of very small as well as large cracks and flaws in the part.

The gel containing the combination of fluorescent dyes of Example 1, had a light yellow coloration but was transparent and the part surface could be viewed through the gel layer.

After testing was completed, the gel layer was removed from the wing skin surface by wiping first with a dry cloth and then with a water moistened wiping cloth. The area from which the gel layer was removed was then viewed under fluorescent or black light, and residual gel on the surface was indicated by very bright fluorescent yellow-green smears. Such residual gel was then removed by a final water spray.

EXAMPLE 17

The procedure of Example 16 above was essentially repeated, but employing as the test part a titanium alloy fusion welded airplane fuselage bulkhead, and employing the gel composition of Example 2 above, the gel being applied to a vertical surface of the bulkhead.

The transducer was pressed into contact with the gel on the vertical surface of the bulkhead, and was moved by sliding in various directions. The variations in noise signals produced by ultrasonic transmission generated by the transducer and transmitted through the test body were observed on the display unit of the ultrasonic test equipment, detecting the location, orientation and size of so-called unbonds of the fusion welds within the part. During the inspection process, it was noted that the transducer could be positioned at any location on the gel disposed on the vertical surface of the part, and the transducer remained in this position without any support by the operator's hand, permitting the operator freedom to make adjustments on the test equipment at will.

Following inspection, the gel was scraped free of the surface of the part by a knife or similar means, after which the part was viewed under black or fluorescent light, with residual traces of the gel indicated by bright yellow smears. The residual gel was then removed from the part surface by water spraying.

EXAMPLE 18

The procedure of Example 16 was essentially followed but employing the gel composition of Example 4, which was applied by spatula on a surface of a steel casting. The gel layer was in the form of a clear transparent gel under visible light, so that the surface of the casting could be seen through the gel layer.

Upon contact with and movement of an ultrasonic probe or transducer of an ultrasonic test equipment over the surface of the part by sliding contact of the probe with the gel surface, microcracks as well as cracks of substantially larger size both in the surface and within the body of the casting were detected by variations in the noise signals transmitted through the body of the part and received by the receiving unit of the test equipment.

After testing, the gel layer was scraped from the surface of the part and returned to the container of gel for reuse, and the surface of the test area then viewed under black light, showed deep blue colorations or smears emitted from the fluorescent dye in those areas containing residual gel. Such residual gel was then removed by water spray.

EXAMPLE 19

The procedure of Example 16 was substantially repeated, but employing the gel composition of Example 3, containing no dye.

In this embodiment, particular care was taken to remove practically all of the gel following ultrasonic inspection, by the wiping procedure of Example 16, leaving essentially no residual gel on the surface of the part.

While I have described particular embodiments of my invention for the purpose of illustration within the spirit of the invention, it will be understood that the invention is not to be taken as limited except by the scope of the appended claims.

I claim:

1. A composition for ultrasonic inspection of surface and subsurface flaws and discontinuities, comprising an aqueous gel containing an N-alkyl-2-pyrrolidone wherein the alkyl group contains from 1 to 4 carbon atoms, a water soluble surfactant and silica suspended in said gel.

2. A composition as defined in claim 1, said pyrrolidone being N-methyl-2-pyrrolidone.

3. A composition as defined in claim 1, said water soluble surfactant being a nonyl phenyl ether of polyethylene glycol.

4. A composition as defined in claim 1, wherein said silica is fumed silica.

5. A composition as defined in claim 1, wherein said pyrrolidone is N-methyl-2-pyrrolidone and said water soluble surfactant is a nonyl phenyl ether of polyethylene glycol.

6. A composition as defined in claim 5, wherein said silica is fumed silica.

7. A composition as defined in claim 1 including a small amount of a dye.

8. A composition as defined in claim 6, including a small amount of a fluorescent dye.

9. A composition for ultrasonic inspection of surface and subsurface flaws and discontinuities, comprising a gel consisting essentially of about 10 to about 40 percent of an N-alkyl-2-pyrrolidone wherein the alkyl group contains from 1 to 4 carbon atoms, about 10 to about 35 percent of a water soluble surfactant, about 10 to about 50 percent water and about 10 to about 40 percent powdered silica distributed in said gel, by weight.

10. A composition as defined in claim 9, said pyrrolidone being N-methyl-2-pyrrolidone.

11. A composition as defined in claim 9, said water soluble surfactant being a nonyl phenyl ether of polyethylene glycol.

12. A composition as defined in claim 9, wherein said pyrrolidone is N-methyl-2-pyrrolidone and said water soluble surfactant is a nonyl phenyl ether of polyethylene glycol, and wherein said water is deionized water.

13. A composition as defined in claim 9, said gel consisting essentially of about 15 to about 35 percent of said pyrrolidone, about 15 to about 30 percent of said water soluble surfactant, about 15 to about 40 percent of deionized water and about 10 to about 25 percent of fumed silica, by weight.

14. A composition as defined in claim 9, including about 0.1 to about 2 percent by weight of a dye.

15. A composition as defined in claim 14, wherein said dye is a fluorescent dye.

16. A composition as defined in claim 13, including about 0.2 to about 1.5 percent by weight of a fluorescent dye.

* * * * *